Figure 1:
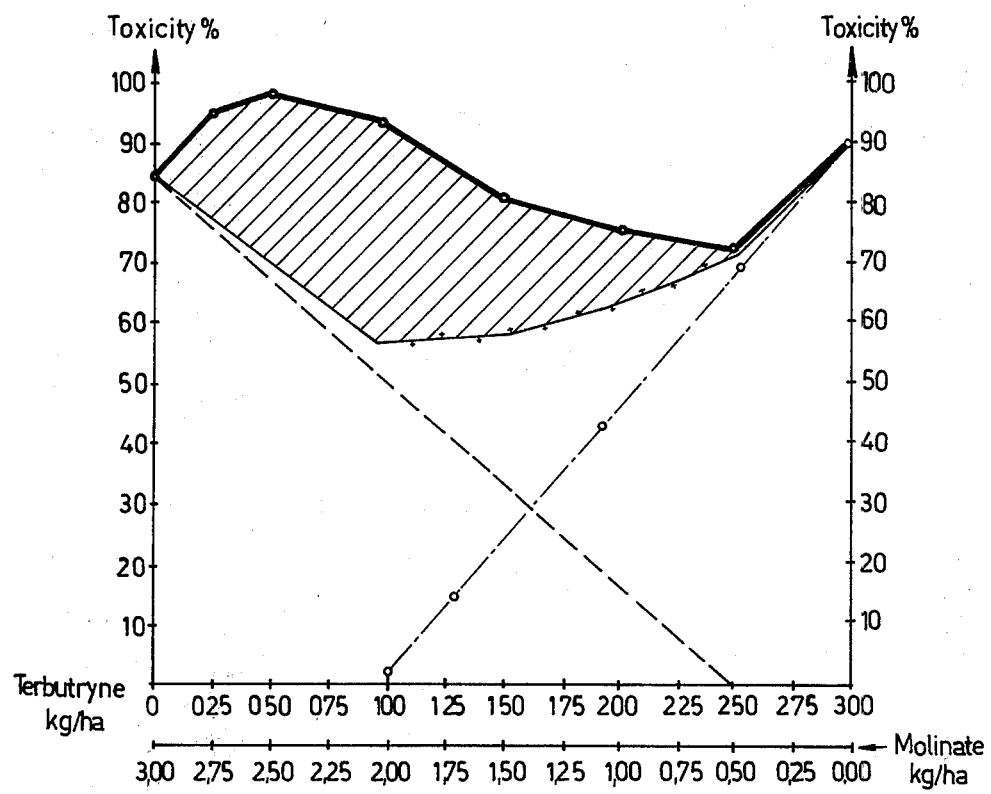

United States Patent [19]

Dombay et al.

[11] 4,220,467

[45] Sep. 2, 1980

[54] COMPOSITION AND METHOD FOR COMBATTING WEEDS IN CEREALS

[75] Inventors: Zsolt Dombay; Erzsébet Grega neé Tóth, both of Miskolc; Ferenc Havelka, Budapest; Anna Kovásznay, Miskolc, all of Hungary

[73] Assignee: Eszakmagyarorszagi Vegyimuvek, Sajobabony, Hungary

[21] Appl. No.: 3,950

[22] Filed: Jan. 16, 1979

[30] Foreign Application Priority Data

Jan. 20, 1978 [HU] Hungary ............................ EA 184

[51] Int. Cl.² .......................... A01N 9/22; A01N 9/00
[52] U.S. Cl. ........................................ 71/93; 71/88; 71/118; 71/120
[58] Field of Search ...................................... 71/88, 93

[56] References Cited

U.S. PATENT DOCUMENTS

| | | | |
|---|---|---|---|
| 3,492,110 | 1/1970 | Hood et al. | 71/93 |
| 3,892,555 | 7/1975 | Pass et al. | 71/93 |
| 3,957,481 | 5/1976 | Bollinger et al. | 71/93 |

FOREIGN PATENT DOCUMENTS

| | | | |
|---|---|---|---|
| 47-29980 | 8/1972 | Japan | 71/88 |
| 50-36637 | 4/1975 | Japan | 71/93 |
| 50-40746 | 4/1975 | Japan | 71/93 |
| 155626 | 12/1975 | Japan | 71/88 |
| 231263 | 10/1967 | U.S.S.R. | 71/88 |

OTHER PUBLICATIONS

Hara et al., "Herbicidal Compositions etc.;" (1974) CA 82 No. 12278 c. (1975).

*Primary Examiner*—Glennon H. Hollrah
*Attorney, Agent, or Firm*—Young & Thompson

[57] ABSTRACT

The invention relates to a composition for combatting weeds in cereals, which contains a (1:2) to (1:5) mixture of 2-tert.-butylamino-4-ethylamino-6-methylthio-1,3,5-triazine and S-ethyl-N,N-hexamethylene-thiocarbamate in an amount of 10 to 80%, along with a conventional carrier, diluent and/or dispersing agent.

The invention relates further to a pre-emergent method of combatting weeds, primarily monocotyledons, in cereals, particularly in winter cereals. According to this method a total amount of 2.0 to 4.5 kg/ha of a (1:2) to (1:5) mixture of 2-tert.-butylamino-4-ethylamino-6-methylthio-1,3,5-triazine and S-ethyl-N,N-hexamethylene-thiocarbamate is applied onto the area to be treated.

4 Claims, 1 Drawing Figure

| | |
|---|---|
| Terbutryne | —·—·—·— |
| Molinate | — — — — |
| Calculated additive toxicity | ——————— |
| Actual toxicity | ——————— |

COMPOSITION AND METHOD FOR COMBATTING WEEDS IN CEREALS

This invention relates to a novel composition for combatting weeds, which comprises a mixture of two known herbicidal agents, i.e. S-ethyl-N,N-hexamethylene-thiocarbamate (further on: Molinate) and 2-tert.-butylamino-4-ethylamino-6-methylthio-1,3,5-triazine (further on: Terbutryne). This composition can be applied to advantage for killing weeds, such as *Avena fatua* and *Apera spice-venti*, which proliferate in cereals.

Chemical methods of combatting weeds have been applied in Hungary for about 25 years in the large-scale cultivation of cereals. According to the existing technology of plant protection, herbicides with hormonal effects are utilized for the post-emergent treatment of cereals sown in the autumn; the herbicides are sprayed onto the sown area in the early spring. The most widespread herbicidal compositions are those containing 2,4-dichlorophenoxyacetic acid (2,4-D) or 2-methyl-4-chlorophenoxyacetic acid (MPCA) as active ingredient.

The prolonged utilization of herbicides with hormonal effects causes, however, a shift in the weed flora of cereals, i.e. it involves an increase in the spreading of monocotyledons resistant towards phenoxyacetic acid derivatives.

Kulkedi (Magyar Mezogazdasag XXXII, No. 13, 12 /1977/) investigated in detail the experiences obtained in the chemical methods for combatting weeds in winter wheat, and pointed out two main disadvantages of the hormonally active agents. One of these disadvantages is that the effectiveness of hormonally active agents is greatly temperature-dependent, thus a favourable effect can be attained only within a narrow temperature range (16° to 22° C.).

The other disadvantage is the substantial change in weed flora, i.e. upon the utilization of these hormonally active agents resistant monocotyledons, such as *Avena fatua* and *Apera spice-venti* has become increasingly widespread.

Publications dealing with chemical methods of combatting weeds in cereals also point out the disadvantages arising from the fact that winter cereals are protected only in the spring. The majority of these publications states that the immediate protection after sowing results in an increase of crop yield, thus they recommend the utilization of pre-emergent treatment methods.

The utilization of pre-emergent treatment methods is further motivated by the fact that wheat is the most sensitive to weed damages in the early stage of development, and the extent of early weediness is of decisive role with regard to the later productivity. When winter wheat is sown in time, a substantial amount of weeds emerges, develops and strengthens even in the autumn. Later on, when winter frosts are over, these weeds start to develop heavily, thus at that time protection can be only of reduced effectiveness.

According to Kulkedi (Novenytermeles 26, No. 4, 299 /1977/) the tests performed in 1974, 1975 and 1976 with nine different types of hormonally active herbicides proved that these agents do not ensure protection against *Avena fatua* and *Apera spice-venti*.

According to the tests of Szekeres (Novenytermeles 26, No. 4, 285 /1977/) Chlortoluron [N'-(3-chloro-4-methylphenyl)-N,N-dimethyl-urea] showed the most potent protecting effect against *Apera spice-venti*, this compound was, however, less active against other weeds, primarily dicotyledons.

It was also recommended to utilize the composition marketed by the firm Shell under the trade name Suffix, containing N-benzoyl-N-(3,4-dichlorophenyl)-aniline as active agent, in the protection of cereals against *Avena fatua*. This composition can be applied onto the area to be protected in the spring as a post-emergent agent. This composition is, indeed, active against *Avena fatua*, the post-emergent utilization is, however, a substantial disadvantage, since in this way the damages arising from the early weediness of winter wheat cannot be eliminated.

Compositions containing 2-tert.-butylamino-4-ethylamino-6-methylthio-1,3,5-triazine (Terbutryne) as active agent have been applied for several years in tests for combatting weeds in cereals (Szekeres: Novenytermeles 26, No. 4, 285 /1977/). This chemical, in a dosage of 4 kg/ha, proved to be effective in combatting dicotyledons which are difficult to kill. For selectivity and security reasons, however, it is not recommended to apply this compound in dosages higher than 3 kg/ha. Even a dosage of 4 kg/ha of the above compound is insufficient, however, to provide safe protection against *Apera spice-venti*, and at least 20% of this week still remains intact after the post-emergent treatment.

It is also known that S-ethyl-N,N-hexamethylene-thiocarbamate (Molinate) is effective in rice cultures against Echinochloa spp. weeds in dosages of 2 to 4 kg/ha (Pesticide Manual, ed. British Crop Protection Council, Fourth Edition, p. 361 /1974/). The active agent can be applied either before planting or after flooding the rice culture.

In our investigations directed to the combatting of resistant monocotyledons (such as *Avena fatua*, *Apera spica-venti*) in cereal cultures, primarily in winter cereal cultures (such as in winter wheat) we have found that complete protection can be attained when applying S-ethyl-N,N-hexamethylene-thiocarbamate (Molinate) in admixture with an appropriate amount of 2-tert.-butylamino-4-ethylamino-6-methylthio-1,3,5-triazine (Terbutryne). According to our experiments the combination of the above two active agents shows a synergistically enhanced effect, since, when applied alone, Molinate exerts a killing effect of only 80% in a dosage of 3 kg/ha and the killing effect of Terbutryne amounts to only 90% also in a dosage of 3 kg/ha, whereas an appropriate combination containing these active agents in a total amount of 3 kg/ha provides a killing effect of 95 to 100%.

The results obtained in testing the herbicidal effects of various combinations of the above two active agents are summarized in the following Tables.

Table 1 indicates the killing effects of the two active agents exerted on *Avena fatua* either alone or in admixture with each other. The tests were performed in cultivation pots. The active agent or combination was applied 10 days after sowing, i.e. a pre-emergent treatment was performed.

Table 1

| Terbutryne | | Molinate | | Combination | | | |
|---|---|---|---|---|---|---|---|
| Dosage kg/ha | Killing effect, % | Dosage kg/ha | Killing effect, % | Terbutryne dosage, kg/ha | Molinate dosage, kg/ha | Total active agent dosage, kg/ha | Killing effect, % |
| — | — | 3.0 | 85.0 | — | — | — | — |
| 0.5 | 0 | 2.5 | 68.0 | 0.5 | 2.5 | 3.0 | 99.0 |
| 1.0 | 1.5 | 2.0 | 51.0 | 1.0 | 2.0 | 3.0 | 93.0 |
| 1.5 | 23.5 | 1.5 | 34.0 | 1.5 | 1.5 | 3.0 | 82.0 |
| 2.0 | 46.0 | 1.0 | 17.0 | 2.0 | 1.0 | 3.0 | 76.0 |
| 2.5 | 68.5 | 0.5 | 0 | 2.5 | 0.5 | 3.0 | 73.0 |
| 3.0 | 90.0 | — | — | — | — | — | — |

The test results listed in Table 1 are also indicated graphically in FIG. 1.

The date of Table 1 and FIG. 1 clearly indicate that Terbutryne exerts a 10% killing effect on *Avena fatua* in a dosage of 1.25 kg/ha; in lower dosages it is completely ineffective. For Molinate a 10% killing effect can be attained with a dosage of 0.75 kg/ha, and the maximum killing effect, appearing at a dosage of 3 kg/ha, is only of 85%.

On the other hand, the appropriate combinations of these two active agents show synergistically enhanced effects, as it appears clearly from the curves of FIG. 1. The domain of synergism corresponds to an (1:5) to (1:2) ratio of Terbutryne and Molinate. The most favourable results can be attained with (1:5) to (1:3) mixtures of the two active agents. As it appears clearly from the curves of FIG. 1, in this domain the combined effect of the two active agents is significantly (by 20 to 30%) greater than the additive value, which proves unambiguously the existence of synergism.

In the further tests we have examined the herbicidal effects of the two active agents on various monocotyledons and dicotyledons. The active agents were applied either alone or in combination with each other, and pre-emergent treatments were performed.

The following weeds were applied in the tests: monocotyledons emerging from seed: *Setaria viridis, Setaria glauca, Poa annua, Avena fatua, Apera spica-venti;* dicotyledons emerging from seed: *Chenopodium album, Amaranthus retroflexus, Viola arvensis, Stellaria media.*

The tests were performed as follows: 100 seeds each of the above weeds were placed into cultivation pots, and the herbicide was applied to the soil on the day after sowing. The active agents were applied as emulsifyable concentrates containing 50% of active agent (see Example 3). Thereafter the cultivation pots were stored in a greenhouse at 10 to 15° C. The number of weeds emerged was determined on the 20th day after the treatment. Parallel tests were performed with untreated controls, and the number of weeds emerged in the treated pots was compared to that observed for the controls. Four replications were applied for each of the individual weeds, and the herbicidal effect was calculated on the basis of the average values. When calculating the herbicidal effect, the average number of the weeds emerged in the treated posts was compared to the average value observed in the control groups. The results, in percentages, are listed in Table 2.

Table 2

| Terbutryne | | | Molinate | | | Combination | | | | |
|---|---|---|---|---|---|---|---|---|---|---|
| Dosage kg/ha | Killing effect, % | | Dosage kg/ha | Killing effect, % | | Terbutryne dosage kg/ha | Molinate dosage kg/ha | Total dosage kg/ha | Killing effect, % | |
| | M | D | | M | D | | | | M | D |
| 0 | — | — | 3.0 | 80 | 30 | — | — | — | — | — |
| 0.5 | 0 | 10 | 2.5 | 58 | 23 | 0.5 | 2.5 | 3.0 | 99 | 95 |
| 1.0 | 1.5 | 30 | 2.0 | 50 | 17 | 1.0 | 2.0 | 3.0 | 94 | 98 |
| 1.5 | 24 | 60 | 1.5 | 41 | 13 | 1.5 | 1.5 | 3.0 | 80 | 90 |
| 2.0 | 40 | 78 | 1.0 | 20 | 5 | 2.0 | 1.0 | 3.0 | 76 | 83 |
| 2.5 | 50 | 85 | 0.5 | 0 | 0 | 2.5 | 0.5 | 3.0 | 74 | 80 |
| 3.0 | 85 | 96 | — | — | — | — | — | — | — | — |

M = monocotyledons
D = dicotyledons

The test results clearly indicate that the combination of 0.5 of Terbutryne and 2.5 kg of Molinate exerts a 99% killing effect on the monocotyledons, whereas the combination of 1 kg of Terbutryne and 2 kg of Molinate has a 94% or 98% killing effect, respectively. At the same time, 0.5 kg of Terbutryne alone has no effect on the monocotyledons tested, and exerts only a 10% killing effect on dicotyledons. When applying Terbutryne alone in a dosage of 1.0 kg, no effect can be observed for monocotyledons, and for dicotyledons the killing effect is only of 30%. In a dosage of 2 kg Molinate exerts a killing effect of 50% on the monocotyledons, whereas its killing effect exerted on dicotyledons is far lower (17%). With a Molinate dosage of 2.5 kg a killing effect of 58% and 23% can be attained for monocotyledons and dicotyledons, respectively.

The data listed in Table 2 also prove that the claimed combination of the two active agents exerts a significantly better killing effect than that of the arithmetical sum of the values observed for the individual active agents, since, as stated before, Terbutryne has no effect on monocotyledons in a dosage below 1.25 kg/ha, and in the same test Molinate has only a 58% killing effect in a dosage of 2.5 kg/ha. In the case of dicotyledons only a 30% killing effect can be attained with 1 kg/ha of Terbutryne, and the killing effect of 2 kg/ha of Molinate amounts to only 17%, whereas the combination of the two active agents with the same individual dosages shows a killing effect of 98%.

Further tests were performed in order to determine the dosage limit of the synergistic combination according to the invention which do not exert phytotoxic effects on cereals. In these tests a 4:1 mixture of Molinate and Terbutryne was applied, and only the dosage was varied.

The tests were performed, like the previous ones, in after the treatment, in order to evaluate the killing effect of the active agent(s) applied. The results are listed in Table 4.

Table 4

| Terbutryne | | | Molinate | | | Combination | | | | |
|---|---|---|---|---|---|---|---|---|---|---|
| | | | | | | Terbutryne | Molinate | Total | | |
| Dosage | Killing effect, % | | Dosage | Killing effect, % | | dosage | dosage | dosage | Killing effect, % | |
| kg/ha | M | D | kg/ha | M | D | kg/ha | kg/ha | kg/ha | M | D |
| — | — | — | 3.0 | 75 | 30 | — | — | — | — | — |
| 0.5 | 0 | 10 | 2.5 | 58 | 25 | 0.5 | 2.5 | 3.0 | 99 | 98 |
| 1.0 | 2 | 34 | 2.0 | 50 | 20 | 1.0 | 2.0 | 3.0 | 98 | 97 |
| 1.5 | 28 | 62 | 1.5 | 38 | 10 | 1.5 | 1.5 | 3.0 | 84 | 90 |
| 2.0 | 48 | 80 | 1.0 | 17 | 0 | 2.0 | 1.0 | 3.0 | 80 | 80 |
| 2.5 | 65 | 90 | 0.5 | 0 | 0 | 2.5 | 0.5 | 3.0 | 73 | 76 |
| 3.0 | 70 | 96 | — | — | — | — | — | — | — | — |

M = monocotyledons
D = dicotyledons cultivating pots with a surface of 4 dm², in four replications. 1000 g of screened brown forest soil was introduced into the individual pots, 100 seeds each of the cultivated plant and weed were placed onto the soil, and the seeds were covered with 500 g. of forest soil. The pots were placed into a greenhouse (temperature: 10° to 15° C., relative humidity: 75 to 98%), and the soil was watered continuously in accordance with the optimum water capacity. The germination ability of the seeds utilized (cereals and weeds) was 95%. The treatment was performed on the 10th day after sowing, utilizing an emulsifyable concentrate with 50% active agent content (see Example 3). The results were evaluated on the 20th day after the treatment, and the activity values were expressed in percentages in relation to the untreated controls. The results are summarized in Table 3.

Table 3

| Dosage of the combination, kg/ha | TOXICITY | | | | Weeds | | | |
|---|---|---|---|---|---|---|---|---|
| | Cereals | | | | Monocot-yledons | | Dicot-yledons | |
| | Wheat | | Barley | | | | | |
| | pre | post | pre | post | pre | post | pre | post |
| 2.0 | 0 | 0 | 0 | 0 | 90 | 85 | 70 | 75 |
| 2.5 | 0 | 0 | 0 | 0 | 98 | 97 | 96 | 95 |
| 3.0 | 0 | 0 | 0 | 0 | 99 | 98 | 95 | 97 |
| 3.5 | 0 | 0 | 0 | 0 | 99 | 98 | 98 | 99 |
| 4.0 | 0 | 0 | 0 | 0 | 100 | 100 | 100 | 100 |
| 4.5 | 5 | 5 | 0 | 0 | 100 | 100 | 100 | 100 |
| 5.0 | 13.5 | 12 | 12.5 | 0 | 100 | 100 | 100 | 100 |

The data of Table 3 show that for wheat the combination tested starts to provoke phytotoxic symptoms at a dosage of 4.5 kg/ha, although at this limiting value only a slight phytotoxicity appears. For barley phytotoxic symptoms appear only at an active agent dosage of 5.0 kg/ha. On the other hand, the effective dosage against weeds is between 2.5 and 4.0 kg/ha, and no significant difference exists between the effects of the individual dosages within this range.

Based on the results of the above tests the combinations according to the invention were also tested in post-emergent treatments. The treatments were performed when the host plant (wheat or barley) was in the 2-3 leaf stage of development. In other respects the method was the same as given in connection with Table 3.

Prior to applying the active agent, the amount of weeds was determined and expressed as percentages in relation to that observed in the pots selected as controls. The same procedure was performed on the 20th day after the treatment, in order to evaluate the killing effect of the active agent(s) applied. The results are listed in Table 4.

The data of Table 4 clearly indicate that the (1:2) to (1:5) mixtures of the two active agents are the most effective also in post-emergent treatments.

Thus the invention relates to a composition for combatting weeds in cereals, which comprises a (1:2) to (1:5) mixture of 2-tert.-butylamino-4-ethylamino-6-methylthio-1,3,5-triazine and S-ethyl-N,N-hexamethylene-thiocarbamate. This composition contains the two active agents in an amount of 10 to 80%, along with a conventional carrier, diluent and/or dispersing agent.

The compositions according to the invention contain the above two active agents preferably in a ratio of (1:3) to (1:5).

The invention relates further to a pre-emergent method of combatting weeds, primarily monocotyledons, in cereals, particularly in winter cereals. In this method a total amount of 2.0 to 4.5 kg/ha of a (1:2) to (1:5) mixture of 2-tert.-butylamino-4-ethylamino-6-methylthio-1,3,5-triazine and S-ethyl-N,N-hexamethylene-thiocarbamate is applied to the area to be treated.

It is preferred to apply the two active agents onto the area to be treated in a pre-formed mixture, particularly as a composition as defined above. One can also apply, however, the two active agents separately onto the area to be treated.

The following Examples illustrate the preparation of herbicidal compositions containing 10 to 80% by weight of the two active agents along with conventional additives, such as carriers, diluents, dispersing agents, etc. The Examples are given only for the purpose of illustration without, however, limiting the scope of the invention to them.

The additives designated in the Examples by the trade name "Atlox" are emulsifying agents produced by the firm Atlas Chemie GmbH, Essen, German Federal Republic. The carrier mentioned under the trade name Attagel, furthermore the emulsifying agent mentioned under the trade name Renex are produced by the firm Atlas Corporation, United States.

EXAMPLE 1

500 g of Molinate, 72 g of Atlox 4857B, 36 g of Atlox 4868B and 12 g of Renex are introduced into a 2500 ml flask equipped with a stirrer, feeder and aerating means. 256 ml of water are added to the mixture under stirring. Thereafter 250 g of Terbutryne are introduced into the flask with stirring, and the resulting homogeneous suspension is ground for one hour on a Fryma MK-95/R type wet grinder adjusted to a grade of 0.1. 12 g of Attagel 40 are added to the suspension, and grinding is continued for an dditional 30 minutes. An aqueous suspension containing 65% of active agent is obtained. This suspension, after diluting it with water, can be sprayed onto the area to be treated in a dosage of 6 kg/ha.

EXAMPLE 2

600 g of Molinate, 66 g of Atlox 4857B, 42 g of Atlox 4868B and 12 g of Renex 30 are introduced into a 2500 ml flask equipped with a stirrer, feeder and aerating means. 220 ml of water are added to the mixture under stirring. Thereafter 200 g of Terbutryne are introduced into the flask with stirring, and the resulting suspension is ground one hour on a Fryma MK-95/R type wet grinder adjusted to grade 0.1. 10 g of Attagel 40 are introduced then, and grinding is continued for an additional 30 minutes.

EXAMPLE 3

40 g of Terbutryne and 160 g of a 2:1 mixture of o-xylene and methylene chloride are introduced into a 1000 ml flask equipped with a stirrer, feeder and aerating means. After 15 minutes of stirring 160 g of Molinate, 28 g of Atlox 4857B and 12 g of Atlox 3400B are introduced, and stirring is continued at room temperature for an additional 15 minutes. The resulting solution is filtered through a folded paper filter. An emulsifiable concentrate containing 50% of active agent is obtained.

EXAMPLE 4

104 g of Molinate, 26 g of Terbutryne, 46 g of water, 8 g of Atlox 4857B and 12 g of Atlox 4868B are introduced into a batchwise operating laboratory bead mill with an effective capacity of 600 ml. 400 g of glass beads (1.5 to 2 mm in diameter) are placed into the mill, and grinding is performed for 2 hours under cooling with a speed of 775 rotations/minute. 15 minutes before finishing the grinding 4 g of Attagel 40 are introduced. After grinding the glass beads are removed by sieving through a sieve with a gap width of 1 mm. A composition containing 65% of active agent is obtained.

EXAMPLE 5

88 g. of Molinate, 44 g of Terbutryne, 44 g of water, 6 g of Atlox 4857B and 14 g of Atlox 4868B are introduced into a batchwise operating laboratory bead mill with an effective capacity of 600 ml. 400 g of glass beads, 1.5 to 2 mm in diameter, are introduced, and grinding is performed for 2 hours under cooling with a speed of 775 rotations/minute. 15 minutes before the end 4 g of Attagel 40 are introduced. After grinding the glass beads are removed by sieving through a sieve with a gap width of 1 mm. A composition containing 65% of active agent is obtained.

EXAMPLE 6

40 g of Terbutryne and 320 g of a 2:1 mixture of o-xylene and methylene chloride are introduced into a 2500 ml flask equipped with a stirrer, feeder and aerating means. After 15 minutes of stirring 160 g of Molinate, 28 g of Atlox 4857B and 12 g of Atlox 3400B are introduced, and stirring is continued for an additional 15 minutes. The resulting mixture is filtered through a folded paper filter. An emulsifiable concentrate containing 25% of active agent is obtained.

The compositions prepared according to the previous Examples can be applied onto the area to be treated by conventional agrochemical methods. One may proceed e.g. by diluting the composition with water to an appropriate concentration and applying the aqueous composition to the area to be treated with a conventional apparatus (such as a spraying device) in an amount corresponding to a total active agent dosage of 2.0 to 4.5 kg/ha.

What we claim is:

1. A composition for combatting weeds in cereals, characterized by containing a (1:2) to (1:5) by weight ratio, mixture of 2-tert.-butylamino-4-ethylamino-6-methylthio-1,3,5-triazine and S-ethyl-N,N-hexamethylene-thiocarbamate in an amount of 10 to 80% by weight, along with an inert conventional carrier, diluent and/or dispersing agent.

2. A composition as claimed in claim 1, characterized by containing the two active agents in a ratio of (1:3) to (1:5).

3. A method of combatting welds, primarily monocotylecons, in winter wheat, characterized by applying a total amount of 2.0 to 4.5 kg/ha of a (1:2) to (1:5) weight ratio mixture of 2-tert.-butylamino-4-ethylamino-6-methylthio-1,3,5-triazine and S-ethyl-N,N-hexamethylene-thiocarbamate onto the area to be treated at a pre-emergent stage of said wheat.

4. A method as claimed in claim 3, characterized by applying the two active agents separately onto the area to be treated.

* * * * *